US012102733B2

(12) United States Patent
Wang et al.

(10) Patent No.: US 12,102,733 B2
(45) Date of Patent: Oct. 1, 2024

(54) PRE-LOADABLE BIOLOGICAL HEART VALVE CAPABLE OF RAPID REHYDRATION AND PREPARATION METHOD THEREOF

(71) Applicants: VENUS MEDTECH (HANGZHOU), INC., Zhejiang (CN); Sichuan University, Chengdu (CN)

(72) Inventors: Yunbing Wang, Chengdu (CN); Gaocan Li, Chengdu (CN); Yang Lei, Chengdu (CN); Li Yang, Chengdu (CN); Hou-Sen Lim, Singapore (SG); Dajun Kuang, Zhejiang (CN); Jincheng Yu, Hangzhou (CN)

(73) Assignees: VENUS MEDTECH (HANGZHOU), INC., Hangzhou (CN); Sichuan University, Chengdu (CN)

( * ) Notice: Subject to any disclaimer, the term of this patent is extended or adjusted under 35 U.S.C. 154(b) by 769 days.

(21) Appl. No.: 17/313,910

(22) Filed: May 6, 2021

(65) Prior Publication Data
US 2021/0268151 A1     Sep. 2, 2021

Related U.S. Application Data

(63) Continuation of application No. PCT/CN2019/105371, filed on Sep. 11, 2019.

(51) Int. Cl.
*A61L 27/36* (2006.01)

(52) U.S. Cl.
CPC ..... *A61L 27/3687* (2013.01); *A61L 2300/214* (2013.01); *A61L 2430/20* (2013.01); *A61L 2430/40* (2013.01)

(58) Field of Classification Search
CPC ........... A61L 27/3687; A61L 2300/214; A61L 2430/20; A61L 2430/40
See application file for complete search history.

(56) References Cited

U.S. PATENT DOCUMENTS

| 4,481,009 | A | * | 11/1984 | Nashef | A61L 27/3687 |
| | | | | | 8/94.11 |
| 5,697,972 | A | | 12/1997 | Kim et al. | |
| 8,142,805 | B1 | * | 3/2012 | Vyavahare | A61L 27/54 |
| | | | | | 424/94.1 |
| 8,748,490 | B2 | | 6/2014 | Dove et al. | |
| 2001/0053839 | A1 | | 12/2001 | Koken | |
| 2020/0000962 | A1 | * | 1/2020 | Alavi | A61L 27/507 |

FOREIGN PATENT DOCUMENTS

| CN | 101947147 A | 1/2011 |
| CN | 105194733 A | 12/2015 |
| CN | 106913909 A | 7/2017 |
| CN | 107007887 A | 8/2017 |
| CN | 109172867 A | 1/2019 |
| WO | WO9804299 A1 | 2/1998 |

OTHER PUBLICATIONS

English translation of CN107007887. (Year: 2017).*
International Search Report and Opinion dated Nov. 27, 2019 for corresponding PCT Application No. PCT/CN2019/105371.
Extended European Search Report dated May 3, 2021 for Corresponding European Application No. 19861856.3.
"Effects of heparin immobilization on the surface characteristics of a biological tissue fixed with a naturally occurring crosslinking agent (genipin): an in vitro study" vol. 22, Issue 6, Mar. 15, 2001, pp. 523-533.

* cited by examiner

*Primary Examiner* — Samuel G Gilbert
(74) *Attorney, Agent, or Firm* — Raymond Sun

(57) ABSTRACT

A method for preparing a pre-loadable biological heart valve capable of rapid rehydration includes performing a cross-linking treatment, wherein a biological valve is cross-linked by soaking in an aqueous glutaraldehyde solution; performing a hydrophilic treatment, wherein the biological valve is soaked in a solution containing a hydrophilic molecule and a condensing agent, to allow the hydrophilic molecule to be immobilized on the biological valve by chemical grafting; and performing a drying treatment, wherein the biological valve after the hydrophilic treatment and the cross-linking treatment is dried to obtain the pre-loadable biological heart valve capable of rapid rehydration.

20 Claims, No Drawings a condensing agent, to allow the hydrophilic molecule to be immobilized on the biological valve by chemical grafting; and a drying treatment, wherein the biological valve after the hydrophilic treatment and the cross-linking treatment is dried to obtain a pre-loadable biological heart valve capable of rapid rehydration.

PRE-LOADABLE BIOLOGICAL HEART VALVE CAPABLE OF RAPID REHYDRATION AND PREPARATION METHOD THEREOF

TECHNICAL FIELD

The present disclosure relates to the field of medical materials and medical devices, and in particular to a pre-loadable biological heart valve capable of rapid rehydration and a preparation method thereof.

BACKGROUND

Prosthetic valve is an artificial organ having the function of a natural heart valve that can be implanted into the heart to replace a heart valve. When the heart valve lesion is severe and cannot be restored or improved by a valve separation or repair surgery, prosthetic heart valve replacement is needed. With the development of technology in the 21st century, the use of transcatheter valve implantation is increasing worldwide. Compared with the traditional surgical valve replacement suffering from high risk, transcatheter aortic biological valve implantation has the potential to reduce mortality and morbidity. Transcatheter valve implantation, as a less traumatic and lower-risk treatment, brings new possibilities to patients with severe aortic valve stenosis, especially those who cannot burden thoracotomy.

At present, the transcatheter interventional biological heart valve products developed in China and other countries are preserved by soaking in glutaraldehyde, and a valve component needs to be mounted to a delivery system at the operation site, which may bring various additional risks to the operation. The research and development of a specially treated "pre-loadable" biological heart valve system has become one of the problems urgent to be solved in clinical use of interventional valves. The pre-loadable biological heart valve needs to be stored in a dry state. Therefore, the ability of the biological heart valve material in the dry state to rehydrate in the water after being crimped becomes an important indicator for evaluating the performance of the pre-loadable valve. The existing biological heart valve material has a hydrophobic structure on its surface and cannot be rehydrated after being dried, and the crease cannot be flattened, causing inconvenience in use.

Therefore, the existing technology needs to be improved and developed.

SUMMARY

In view of the above-mentioned shortcomings existing in the prior art, an objective of the present disclosure is to provide a pre-loadable biological heart valve capable of rapid rehydration and a preparation method thereof, to solve the problem that the existing interventional biological valve cannot be rehydrated after being dried, and the crease cannot be flattened, causing inconvenience in use.

The technical solution adopted in the present disclosure is as follows.

The present disclosure provides a preparation method of the pre-loadable biological heart valve capable of rapid rehydration, which includes:

a cross-linking treatment, wherein a biological valve is cross-linked by soaking in an aqueous glutaraldehyde solution;

a hydrophilic treatment, wherein the biological valve is soaked in a solution containing a hydrophilic molecule According to the method for preparing a pre-loadable tissue heart valve capable of rapid rehydration, the hydrophilic molecule is a hydrophilic molecule containing an amino group or a carboxyl group.

According to the method for preparing a pre-loadable tissue heart valve capable of rapid rehydration, the hydrophilic molecule includes one or more of sodium glycinate, sodium alanine, sodium lysine, sodium glutamate, sodium aspartate, aminoethanol, tromethamine and diglycolamine.

According to the method for preparing a pre-loadable tissue heart valve capable of rapid rehydration, the hydrophilic molecule includes one or more of α-aminopolyethylene glycol, polyethyleneimine, polyacrylic acid, and α-carboxypolyethylene glycol, water-soluble chitosan, sodium alginate, hyaluronic acid, polyglycine, polyalanine, polylysine, polyglutamic acid, polyarginine, collagen and gelatin.

According to the method for preparing a pre-loadable tissue heart valve capable of rapid rehydration, the condensing agent includes dicyclohexyl carbodiimide, N-hydroxysuccinimide, 1-(3-dimethylaminopropyl)-3-ethyl carbodiimide, or 1-hydroxybenzotriazole; and the concentration of the condensing agent is 0.1 to 20% by weight.

According to the method for preparing a pre-loadable tissue heart valve capable of rapid rehydration, in the hydrophilic treatment step, the concentration of the hydrophilic molecule in the solution is 5 to 50% by weight.

According to the method for preparing a pre-loadable tissue heart valve capable of rapid rehydration, in the hydrophilic treatment step, the reaction temperature for the chemical grafting is 4 to 37° C., and the reaction time is 1 to 7 days.

According to the method for preparing a pre-loadable tissue heart valve capable of rapid rehydration, in the cross-linking treatment step, the concentration of glutaraldehyde is 0.1 to 10% by volume.

According to the method for preparing a pre-loadable tissue heart valve capable of rapid rehydration, in the cross-linking treatment step, the temperature for the cross-linking reaction is 4 to 37° C., and the reaction time is 1 to 7 days.

According to the method for preparing a pre-loadable tissue heart valve capable of rapid rehydration, in the drying treatment step, the drying temperature is 4 to 50° C., and the drying time is 1 to 7 days.

According to the method for preparing a pre-loadable tissue heart valve capable of rapid rehydration, the cross-linking treatment is performed first, then the hydrophilic treatment is performed, and finally the drying treatment is performed; or, the hydrophilic treatment is performed first, then the cross-linking treatment is performed, and finally the drying treatment is performed.

According to the method for preparing a pre-loadable tissue heart valve capable of rapid rehydration, before and after the cross-linking treatment, at least one hydrophilic treatment is performed, and finally, the drying treatment is performed.

According to the method for preparing a pre-loadable tissue heart valve capable of rapid rehydration, further includes a step of washing the biological valve before the cross-linking treatment and the hydrophilic treatment.

According to the method for preparing a pre-loadable tissue heart valve capable of rapid rehydration, the step of washing the biological valve includes: washing a fresh biological valve with deionized water at 3 to 5° C. with shaking at 80 to 120 rpm for 1.5 to 3 hrs.

According to the method for preparing a pre-loadable tissue heart valve capable of rapid rehydration, the tissue valve is a porcine or bovine pericardium.

The present disclosure also provides a pre-loadable tissue heart valve capable of rapid rehydration, which is prepared by the preparation method as described above.

Beneficial effects of the embodiments are as follows. The present disclosure provides a pre-loadable tissue heart valve capable of rapid rehydration and a preparation method thereof. The pre-loadable tissue heart valve prepared by the preparation method of the present disclosure can achieve rapid rehydration, and the crease can be quickly flattened after rehydration, bringing convenience during use.

DESCRIPTION OF THE EMBODIMENTS

The present disclosure provides a pre-loadable biological heart valve capable of rapid rehydration and a preparation method thereof. To make the objective, technical solution and effect of the present disclosure clearer, the present disclosure will be described in further detail below. It should be understood that the specific examples described herein are merely provided for illustrating, but not to limit the present disclosure.

A preferred embodiment of the present disclosure provides a preparation method of the pre-loadable biological heart valve capable of rapid rehydration, that is, a method for hydrophilically treating a pre-loadable biological heart valve which includes the following steps:

a cross-linking treatment, wherein a biological valve is cross-linked by soaking in an aqueous glutaraldehyde solution;

a hydrophilic treatment, wherein the biological valve is soaked in a solution containing a hydrophilic molecule and a condensing agent, to allow the hydrophilic molecule to be immobilized on the biological valve by chemical grafting; and a drying treatment, wherein the biological valve after the hydrophilic treatment and the cross-linking treatment is dried to obtain a pre-loadable biological heart valve capable of rapid rehydration.

The untreated biological valve material has a hydrophobic structure on its surface and thus is able to be rehydrated after being dried, and the crease cannot be flattened. In the present disclosure, it is creative to make the hydrophilic molecule be immobilized on the biological heart valve by chemical grafting before and after the biological valve tissue is cross-linked with glutaraldehyde, to allow the biological heart valve has the ability of rapid rehydration.

Further, in this embodiment, the sequence of each step in the preparation method includes the following. 1) The cross-linking treatment is performed first, then the hydrophilic treatment is performed, and finally the drying treatment is performed, that is, the hydrophilic treatment takes place after the cross-linking with glutaraldehyde. 2) The hydrophilic treatment is performed first, then the cross-linking treatment is performed, and finally the drying treatment is performed, that is, the hydrophilic treatment takes place before the cross-linking with glutaraldehyde. 3) Preferably, at least one hydrophilic treatment is performed respectively before and after the cross-linking with glutaraldehyde, and finally the drying treatment is performed, that is, the treatment is repeated several times before and after the cross-linking with glutaraldehyde.

Further, in this embodiment, the biological valve mentioned in the present disclosure includes but is not limited to porcine pericardium, bovine pericardium and the like. Before the cross-linking treatment and the hydrophilic treatment, the method also includes the step of washing the animal pericardium. The washing process may include: collecting fresh porcine or bovine pericardial tissue and storing it at a low temperature of 4° C. in a wet state. The pericardial tissue is washed with deionized water (distilled water) by gentle friction under a fluid pressure with shaking to remove the attached non-pericardial and non-collagen tissues. The washing in the present disclosure achieves effective cell removal from the pericardial tissue through osmotic shock, and preferably the washing continues until no attached non-pericardial or non-collagen tissue is observed. In an embodiment, preferably, the step of washing the animal pericardium includes: washing the fresh animal pericardium with deionized water at 3 to 5° C. with shaking at 80 to 120 rpm for 1.5 to 3 hrs. For example, it can be washed with deionized water at 4° C. with shaking at 100 rpm for 2 hrs, and then the washed fresh animal (porcine or bovine) pericardium is cross-linked or subjected to the hydrophilic treatment.

Further, in this embodiment, the hydrophilic molecule is preferably a hydrophilic molecule containing an amino group or a carboxyl group, and the grafted hydrophilic molecule includes a hydrophilic small molecule and a hydrophilic polymer. In case that the hydrophilic molecule is a hydrophilic small molecule, it includes, but is not limited to, one or more of sodium glycinate, sodium alanine, sodium lysine, sodium glutamate, sodium aspartate, aminoethanol, tromethamine and diglycolamine. In case that the hydrophilic molecule is a hydrophilic polymer, it includes, but is not limited to, one or more of α-aminopolyethylene glycol, polyethyleneimine, polyacrylic acid, α-carboxypolyethylene glycol, water-soluble chitosan, sodium alginate, hyaluronic acid, polyglycine, polyalanine, polylysine, polyglutamic acid, polyarginine, collagen and gelatin. The condensing agent includes, but is not limited to, dicyclohexyl carbodiimide (DCC), N-hydroxysuccinimide (NHS), 1-(3-dimethylaminopropyl)-3-ethyl carbodiimide (EDC), or 1-hydroxybenzotriazole (HOBt).

Further, in this embodiment, in the hydrophilic treatment step, the concentration (weight percentage concentration) of the condensing agent in the solution is preferably 0.1 to 20%, for example, 0.1%. 1%. 5%, 10%. 15%, or 20%, etc. The concentration (weight percentage concentration) of the hydrophilic molecules is preferably 5 to 50%, for example, 5%. 13%, 30%, or 50%, etc. In the hydrophilic treatment step, the reaction temperature for the chemical grafting is 4 to 37° C., and the reaction time is 1 to 7 days. This step ensures that as many hydrophilic molecules are grafted as possible.

Further, in this embodiment, the concentration of the aqueous glutaraldehyde solution is preferably 0.1 to 10% by volume, for example, 0.1%. 1%. 5%, or 10%, etc., and the pH of the aqueous glutaraldehyde solution is preferably 7 to 8, for example, 7, 7.4, or 8 etc. Preferably, in the cross-linking treatment step, the temperature for the cross-linking reaction is 4 to 37° C. and the reaction time is 1 to 7 days. This step is cross-linking of the biological valve, and will achieve stable cross-linking of most collagen tissues, to improve the structural stability of the entire pericardial tissue, and reduce or eliminate the immunogenicity.

Further, in this embodiment, in the drying treatment step, the drying temperature is 4 to 50° C., and the drying time is 1 to 7 days. The biological heart valve after the hydrophilic treatment and the cross-linking treatment is thoroughly dried, to obtain the pre-loadable biological heart valve capable of rapid rehydration.

An embodiment of the present disclosure also provides a pre-loadable biological heart valve capable of rapid rehydration, which is prepared by the preparation method as described above. The pre-loadable biological heart valve prepared by the preparation method of the present disclosure achieves rapid rehydration; the crease of which can be quickly flattened after rehydration, and it is easy to operate. The pre-loadable biological heart valve prepared in the present disclosure has excellent mechanical properties and biocompatibility, can simplify the clinical use flow of the valve, shorten the operation time, and reduce the operation risk.

The present disclosure is described in detail by way of specific examples as follows.

Example 1

The specific implementation steps were as follows. 1) The porcine pericardial valve was washed with deionized water, soaked in an aqueous solution of 50% polyglutamic acid and 1% condensing agent at 4° C. for 2 days. 2) Then the porcine pericardial valve was soaked in a 5% glutaraldehyde solution at 4° C. for 7 days. 3) Subsequently, the porcine pericardial valve was soaked in a 50% α-aminopolyethylene glycol aqueous solution at 4° C. for 2 days. 4) The porcine pericardial valve was washed with deionized water, and dried at 37° C. for 1 day to obtain the target pre-loadable biological heart valve material.

After test, it is found that the dried prosthetic biological heart valve prepared in this example can achieve rapid rehydration, and the crease can be quickly flattened after rehydration. Moreover, it can still retain good flexibility in the dry state and has excellent mechanical properties and biocompatibility.

Example 2

The specific implementation steps were as follows. 1) The bovine pericardial valve was washed with deionized water, soaked in an aqueous solution of 50% polyglutamic acid and 5% condensing agent at 4° C. for 2 days. 2) Then the porcine pericardial valve was soaked in a 5% glutaraldehyde solution at 4° C. for 7 days. 3) Subsequently, the porcine pericardial valve was soaked in a 50% α-aminopolyethylene glycol aqueous solution at 4° C. for 2 days. 4) The porcine pericardial valve was washed with deionized water, and dried at 37° C. for 3 days to obtain the target pre-loadable biological heart valve material.

After test, it is found that the dried prosthetic biological heart valve prepared in this example can achieve rapid rehydration, and the crease can be quickly flattened after rehydration. Moreover, it can still retain good flexibility in the dry state and has excellent mechanical properties and biocompatibility.

Example 3

The specific implementation steps were as follows. 1) The porcine pericardial valve was washed with deionized water, soaked in a 5% glutaraldehyde solution at 4° C. for 7 days. 2) Then the porcine pericardial valve was soaked in an aqueous solution of 50% polyglutamic acid and 5% condensing agent at 4° C. for 5 days. 3) Subsequently, the porcine pericardial valve was soaked in a 50% α-aminopolyethylene glycol aqueous solution at 4° C. for 5 days. 4) The porcine pericardial valve was washed with deionized water, and dried at 37° C. for 5 days to obtain the target pre-loadable biological heart valve material.

After test, it is found that the dried prosthetic biological heart valve prepared in this example can achieve rapid rehydration, and the crease can be quickly flattened after rehydration. Moreover, it can still retain good flexibility in the dry state and has excellent mechanical properties and biocompatibility.

Example 4

The specific implementation steps were as follows. 1) The porcine pericardial valve was washed with deionized water, soaked in an aqueous solution of 10% hyaluronic acid and 5% condensing agent at 37° C. for 3 days. 2) Then the porcine pericardial valve was soaked in a 5% glutaraldehyde solution at 4° C. for 7 days. 3) Subsequently, the porcine pericardial valve was soaked in a 50% polyethyleneimine aqueous solution at 37° C. for 3 days. 4) The porcine pericardial valve was washed with deionized water, and dried at 50° C. for 7 days to obtain the target pre-loadable biological heart valve material.

After test, it is found that the dried prosthetic biological heart valve prepared in this example can achieve rapid rehydration, and the crease can be quickly flattened after rehydration. Moreover, it can still retain good flexibility in the dry state and has excellent mechanical properties and biocompatibility.

Example 5

The specific implementation steps were as follows. 1) The porcine pericardial valve was washed with deionized water, soaked in an aqueous solution of 30% sodium alginate and 10% condensing agent at 4° C. for 3 days. 2) Then the porcine pericardial valve was soaked in a 5% glutaraldehyde solution at 4° C. for 7 days. 3) Subsequently, the porcine pericardial valve was soaked in a 40% chitosan aqueous solution at 4° C. for 3 days. 4) The porcine pericardial valve was washed with deionized water, and dried at 4° C. for 4 days to obtain the target pre-loadable biological heart valve material.

After test, it is found that the dried prosthetic biological heart valve prepared in this example can achieve rapid rehydration, and the crease can be quickly flattened after rehydration. Moreover, it can still retain good flexibility in the dry state and has excellent mechanical properties and biocompatibility.

Example 6

The specific implementation steps were as follows. 1) The porcine pericardial valve was washed with deionized water, soaked in an aqueous solution of 50% sodium alginate and 1% condensing agent at room temperature for 5 days. 2) Then the porcine pericardial valve was soaked in a 5% glutaraldehyde solution at 37° C. for 7 days. 3) Subsequently, the porcine pericardial valve was soaked in a 50% chitosan aqueous solution at room temperature for 5 days. 4) The porcine pericardial valve was washed with deionized water, and dried at 37° C. for 6 days to obtain the target pre-loadable biological heart valve material.

After test, it is found that the dried prosthetic biological heart valve prepared in this example can achieve rapid rehydration, and the crease can be quickly flattened after rehydration. Moreover, it can still retain good flexibility in the dry state and has excellent mechanical properties and biocompatibility.

In summary, the present disclosure provides a pre-loadable biological heart valve capable of rapid rehydration and a preparation method thereof. The pre-loadable biological heart valve prepared by the preparation method of the present disclosure can achieve rapid rehydration; the crease of which can be quickly flattened after rehydration, and it is easy to operate. The pre-loadable biological heart valve prepared in the present disclosure has excellent mechanical properties and biocompatibility, can simplify the clinical use flow of the valve, shorten the operation time, and reduce the operation risk.

It is to be understood that the present disclosure is not limited to the above embodiments, modifications and variations can be made by those skilled in the art in accordance with the above description, which shall be covered in the protection scope of the appended claims.

What is claimed is:

1. A method for preparing a pre-loadable biological heart valve capable of rapid rehydration, comprising:
   performing a cross-linking treatment, wherein a biological valve is cross-linked by soaking in an aqueous glutaraldehyde solution;
   performing a hydrophilic treatment, wherein the biological valve is soaked in a solution containing a hydrophilic molecule and a condensing agent, to allow the hydrophilic molecule to be immobilized on the biological valve by chemical grafting; and
   performing a drying treatment, wherein the biological valve after the hydrophilic treatment and the cross-linking treatment is dried to obtain the pre-loadable biological heart valve capable of rapid rehydration;
   wherein the cross-linking treatment is performed and completed first, then the hydrophilic treatment is performed, and finally the drying treatment is performed; or, the hydrophilic treatment is performed and completed first, then the cross-linking treatment is performed, and finally the drying treatment is performed.

2. The method for preparing a pre-loadable biological heart valve capable of rapid rehydration according to claim 1, wherein the hydrophilic molecule is a hydrophilic molecule containing an amino group or a carboxyl group.

3. The method for preparing a pre-loadable biological heart valve capable of rapid rehydration according to claim 2, wherein the hydrophilic molecule comprises one or more of sodium glycinate, sodium alanine, sodium lysine, sodium glutamate, sodium aspartate, aminoethanol, tromethamine and diglycolamine.

4. The method for preparing a pre-loadable biological heart valve capable of rapid rehydration according to claim 2, wherein the hydrophilic molecule comprises one or more of α-aminopolyethylene glycol, polyethyleneimine, polyacrylic acid, and α-carboxypolyethylene glycol, water-soluble chitosan, sodium alginate, hyaluronic acid, polyglycine, polyalanine, polylysine, polyglutamic acid, polyarginine, collagen and gelatin.

5. The method for preparing a pre-loadable biological heart valve capable of rapid rehydration according to claim 1, wherein the condensing agent comprises dicyclohexyl carbodiimide, N-hydroxysuccinimide, 1-(3-dimethylaminopropyl)-3-ethyl carbodiimide, or 1-hydroxybenzotriazole; and of the condensing agent has a concentration in a range of 0.1 to 20% by weight.

6. The method for preparing a pre-loadable biological heart valve capable of rapid rehydration according to claim 1, wherein in the hydrophilic treatment step, the hydrophilic molecule in the solution has a concentration in a range of 5 to 50% by weight.

7. The method for preparing a pre-loadable biological heart valve capable of rapid rehydration according to claim 6, wherein in the hydrophilic treatment step, a reaction temperature for the chemical grafting is in a range of 4 to 37° C., and a reaction time is in a range of 1 to 7 days.

8. The method for preparing a pre-loadable biological heart valve capable of rapid rehydration according to claim 1, wherein in the cross-linking treatment step, glutaraldehyde in the aqueous glutaraldehyde solution has a concentration in a range of 0.1 to 10% by volume.

9. The method for preparing a pre-loadable biological heart valve capable of rapid rehydration according to claim 8, wherein in the cross-linking treatment step, a temperature for the cross-linking treatment is in a range of 4 to 37° C., and a reaction time is in a range of 1 to 7 days.

10. The method for preparing a pre-loadable biological heart valve capable of rapid rehydration according to claim 1, wherein in the drying treatment step, a drying temperature is in a range of 4 to 50° C., and a drying time is in a range of 1 to 7 days.

11. The method for preparing a pre-loadable biological heart valve capable of rapid rehydration according to claim 1, wherein the method further comprises a step of washing the biological valve before the cross-linking treatment and the hydrophilic treatment.

12. The method for preparing a pre-loadable biological heart valve capable of rapid rehydration according to claim 11, wherein the step of washing the biological valve comprises: washing a fresh biological valve with deionized water at 3 to 5° C. with shaking at 80 to 120 rpm for 1.5 to 3 hrs.

13. A method for preparing a pre-loadable biological heart valve capable of rapid rehydration, comprising:
   performing a cross-linking treatment, wherein a biological valve is cross-linked by soaking in an aqueous glutaraldehyde solution;
   before and after the cross-linking treatment, performing at least one hydrophilic treatment, wherein in the hydrophilic treatment, the biological valve is soaked in a solution containing a hydrophilic molecule and a condensing agent, to allow the hydrophilic molecule to be immobilized on the biological valve by chemical grafting; and
   finally performing a drying treatment, wherein the biological valve after the hydrophilic treatment and the cross-linking treatment is dried to obtain the pre-loadable biological heart valve capable of rapid rehydration.

14. The method for preparing a pre-loadable biological heart valve capable of rapid rehydration according to claim 13, wherein the hydrophilic molecule is a hydrophilic molecule containing an amino group or a carboxyl group.

15. The method for preparing a pre-loadable biological heart valve capable of rapid rehydration according to claim 14, wherein the hydrophilic molecule comprises one or more of sodium glycinate, sodium alanine, sodium lysine, sodium glutamate, sodium aspartate, aminoethanol, tromethamine and diglycolamine.

16. The method for preparing a pre-loadable biological heart valve capable of rapid rehydration according to claim 14, wherein the hydrophilic molecule comprises one or more of α-aminopolyethylene glycol, polyethyleneimine, polyacrylic acid, and α-carboxypolyethylene glycol, water-soluble chitosan, sodium alginate, hyaluronic acid, polyglycine, polyalanine, polylysine, polyglutamic acid, polyarginine, collagen and gelatin.

17. The method for preparing a pre-loadable biological heart valve capable of rapid rehydration according to claim 13, wherein the condensing agent comprises dicyclohexyl carbodiimide, N-hydroxysuccinimide, 1-(3-dimethylaminopropyl)-3-ethyl carbodiimide, or 1-hydroxybenzotriazole; and the condensing agent has a concentration in a range of 0.1 to 20% by weight.

18. The method for preparing a pre-loadable biological heart valve capable of rapid rehydration according to claim 13, wherein in the hydrophilic treatment step, the hydrophilic molecule in the solution has a concentration in a range of 5 to 50% by weight, a reaction temperature for the chemical grafting is in a range of 4 to 37° C., and a reaction time is in a range of 1 to 7 days.

19. The method for preparing a pre-loadable biological heart valve capable of rapid rehydration according to claim 13, wherein in the cross-linking treatment step, glutaraldehyde in the aqueous glutaraldehyde solution has a concentration in a range of 0.1 to 10% by volume, a temperature for the cross-linking treatment is in a range of 4 to 37° C., and a reaction time is in a range of 1 to 7 days.

20. The method for preparing a pre-loadable biological heart valve capable of rapid rehydration according to claim 13, wherein in the drying treatment step, a drying temperature is in a range of 4 to 50° C., and a drying time is in a range of 1 to 7 days.

* * * * *

UNITED STATES PATENT AND TRADEMARK OFFICE
CERTIFICATE OF CORRECTION

| | | |
|---|---|---|
| PATENT NO. | : 12,102,733 B2 | Page 1 of 1 |
| APPLICATION NO. | : 17/313910 | |
| DATED | : October 1, 2024 | |
| INVENTOR(S) | : Wang et al. | |

It is certified that error appears in the above-identified patent and that said Letters Patent is hereby corrected as shown below:

On the Title Page

Item [30], insert:
--Foreign Priority Application Data
Sept. 19, 2018 (CN) ............... 201811095787.9--

Signed and Sealed this
Eighteenth Day of March, 2025

Coke Morgan Stewart
*Acting Director of the United States Patent and Trademark Office*